United States Patent [19]
Nollet et al.

[11] Patent Number: 5,043,089
[45] Date of Patent: Aug. 27, 1991

[54] P-SULPHOPHENYL ALKYL CARBONATES AND DETERGENT COMPOSITIONS AND DETERGENT ADDITIVES CONTAINING THESE COMPOUNDS

[75] Inventors: Andreas J. H. Nollet, Hilversum; John Meijer, Deventer; Johannes W. A. Overkamp, Raalte, all of Netherlands

[73] Assignee: Akzo N.V., Netherlands

[21] Appl. No.: 860,585

[22] Filed: May 7, 1986

[30] Foreign Application Priority Data

May 7, 1985 [NL] Netherlands ................. 8501295

[51] Int. Cl.$^5$ ............... C07C 69/90; C11D 3/34; D06L 3/02
[52] U.S. Cl. .................. 252/95; 252/89.1; 252/99; 252/539; 252/558; 252/186.38; 558/268; 558/271
[58] Field of Search ........... 252/99, 95, 539, 558, 252/540, 186.41, 89.1, 182.11, 186.38, 94; 558/268, 271; 560/129

[56] References Cited

U.S. PATENT DOCUMENTS

| | | | |
|---|---|---|---|
| 3,256,198 | 6/1966 | Matzner . | |
| 3,272,750 | 9/1966 | Chase ................... | 252/99 |
| 4,412,934 | 11/1983 | Chung et al. ........... | 252/186.38 |
| 4,486,327 | 12/1984 | Murphy et al. . | |
| 4,681,592 | 7/1987 | Hardy et al. ........... | 8/111 |
| 4,686,061 | 8/1987 | Noltet et al. ........... | 252/89.1 |

FOREIGN PATENT DOCUMENTS

0120591 10/1984 European Pat. Off. .
0166571 1/1986 European Pat. Off. .

Primary Examiner—Josephine Barr
Attorney, Agent, or Firm—Oliff & Berridge

[57] ABSTRACT

The present disclosure relates to novel p-sulphophenyl alkyl carbonates, wherein the alkyl group contains 6 to 10 carbon atoms. These compounds are suitable bleaching activators. Also disclosed are detergent additives and detergent compositions containing these compounds.

12 Claims, No Drawings

P-SULPHOPHENYL ALKYL CARBONATES AND DETERGENT COMPOSITIONS AND DETERGENT ADDITIVES CONTAINING THESE COMPOUNDS

The invention relates to a compound of the general structural formula

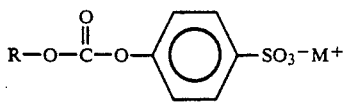 (I)

where R is an alkyl group and M+ represents a cation. The invention also relates to compositions in which this compound is used as bleaching activator.

A compound of the type indicated above and similar compositions are disclosed in U.S. Pat. No. 3,272,750. It describes the use of such a compound as bleaching activator in combination with conventional bleaching agents, such as percarbonate and perborate in order to obtain sufficient bleaching action in the removal of stains from textile materials at a temperature of 60° C. or lower, as usually applied in modern washing machines; at such a temperature the conventional bleaching agents are not or are insufficiently active without the use of activators. Said patent specification describes bleaching activators of the general formula $R_1O.CO.OR_2$, where $R_1$ represents an electron attracting group and $R_2$ is a substituted or unsubstituted alkyl group, aryl group or alicyclic group. Examples are given in it of a few sodium p-sulphophenyl alkyl carbonates, viz. those in which the alkyl group is methyl, ethyl, n-propyl or n-butyl.

The invention has for an object to provide novel compounds of the class of the p-sulphophenyl alkyl carbonates which as compared with the p-sulphophenyl alkyl carbonates known from the above-mentioned United States Patent Specification are more effective bleaching activators. The compound according to the invention is characterized in that the alkyl group R contains 6 to 10 carbon atoms, with the proviso that the $C_6$-alkyl group is n-hexyl.

The earlier, non-prepublished European Patent Application No. 0,166,571 describes a great many bleaching activators, including a few of the general formula $RO.CO.OC_6H_4SO_3M$, R being only defined in general terms as a $C_6$-$C_{20}$ alkyl group. It does not disclose any compounds of the present invention.

It should be added that U.S. Pat. No. 4,412,934 discloses bleaching activators of the general formula $R.CO.OC_6H_4SO_3M$, wherein R is a linear alkyl chain containing from about 5 to about 9 carbon atoms. As to these ester compounds it is demonstrated in European Patent Application No. 0,120,591 that, under certain conditions, they produce odours in the wash solution which are aesthetically unattractive. It is suggested that this problem be solved by employing similar esters having a non-linear aliphatic group R. Another suggestion to solve the same problem is described in U.S. Pat. No. 4,486,327, wherein the use is mentioned of certain alpha substituted derivatives of $C_6$-$C_{18}$ carboxylic acid esters. As substituents Cl, $OCH_3$ and $OC_2H_5$ are disclosed. Those compounds, however, are difficult to prepare.

The present invention provides an effective and a much simpler solution to the same problem and relates to carbonates of the above formula I, wherein R represents an alkyl group containing 6 to 10 carbon atoms, with the proviso that the $C_6$-alkyl group is n-hexyl.

The alkyl group in the present compound may be linear or branched. Examples of such alkyl groups include n-hexyl, n-octyl, 2-ethylhexyl, 3,5,5-trimethylhexyl and n-decyl. Examples of suitable cations M+ are alkali metal ions and the ammonium ion. Preferably, M+ represents a sodium ion or a potassium ion.

The present compounds may be prepared in a known manner by converting an aliphatic alcohol with phosgene into a chloroformate, which is subsequently reacted with 4-hydroxy benzene sulphonic acid in the presence of for example, sodium hydroxide to form the carbonate. Also mixtures of alcohols may be used as the starting material. As examples of suitable mixtures there are mentioned the products marketed by Shell Co. under the trade names of Linevol 79 (a mixture of 47% $C_7$-alcohol, 36% $C_8$-alcohol and 17% $C_9$-alcohol) and Linevol 911 (a mixture of 19% $C_9$-alcohol, 48% $C_{10}$-alcohol and 33% $C_{11}$-alcohol).

As mentioned above, the compound according to the invention is an effective bleach activator. The compound is therefore advantageously incorporated into a detergent composition which, in addition to the bleach activator, contains a bleaching agent, which under alkaline conditions generates hydrogen peroxide, and a surfactant. Also mixtures of the present compounds may be used to that end. Particularly favourable results are obtained using sodium p-sulphophenyl n-hexyl carbonate, sodium p-sulphophenyl 2-ethylhexyl carbonate, sodium p-sulphophenyl n-octyl carbonate and the sodium p-sulphophenyl carbonates derived from the above-mentioned mixtures of Linevol alcohols.

The amount of bleaching activator in the present detergent composition is preferably so chosen that the molar ratio to the activator of the hydrogen peroxide latent in the bleaching agent is at least 1:1.

Examples of suitable, commonly used bleaching agents include alkali metal percarbonate, perborate, persilicate and perpyrophosphate.

Suitable surfactants for use in the present composition are the anionic, non-ionic and amphoteric surface active agents generally employed for this purpose. As examples thereof may be mentioned soaps of synthetic and natural fatty acids, alkyl benzene sulphonates, aliphatic sulphonates, fatty alcohol sulphates, sulphates of alkoxylated fatty alcohols, addition products of ethylene oxide to fatty alcohols, ethylene oxide/propylene oxide copolymers and carboxyl group-, sulphate group- or sulphonate-group-containing betaines. In addition to a bleaching agent, a bleaching activator and a detergent, the present composition may contain the additives usually employed for detergent compositions, such as sequestering agents, fillers, builders, enzymes, fluorescent and optical brightening or whitening agents, dirt suspending agents and foam suppressors.

In actual practice the detergent composition according to the invention may be in a form varying from powdered to granular and may be prepared by methods known in the art, such as crystallization or spray drying of an aqueous slurry or mechanical mixing of the substances. The bleaching activator according to the invention may be applied as such or while provided on a carrier material. Examples of suitable carrier materials are sodium chloride, potassium chloride and sodium sulphate. The invention, however, is not confined to solid detergent compositions but also comprises liquid detergent compositions containing the present bleaching activators.

The present bleaching activator may also be added separately, in the form of a detergent additive containing the bleach activator, to aqueous wash liquor containing at least a surfactant and a hydrogen peroxide generating bleaching agent. To this end the bleaching activator may be applied in the form of powder, preferably provided on a carrier, such as sodium chloride, potassium chloride or sodium sulphate or in the form of a solution or dispersion. The bleaching activator may also be used in the form of a coated particle; examples of suitable coating materials are ethoxylated fatty acids and poly(ethylene oxide). Alternatively, the bleaching activator may have been introduced into a sachet or combined with a flexible substrate, as described for acyl group-containing bleaching activators in European Patent Application No. A1-120591. Such a detergent additive may also contain mixtures of the present bleaching activators and other active washing agents. As far as the latter agents are concerned it should of course be noted that the choice of them is dependent on the compatibility with the present activator. This is of special importance when the additive is used in the form of a solution or dispersion.

The present examples serve to illustrate the invention. All percentages in them are by weight.

EXAMPLE 1

In this example a description is given of a general procedure used for preparing the present compounds. The table below gives the reaction conditions and the reaction results for three compounds.

To a stirred solution in 30 g of water of 0.1 mole of 4-hydroxybenzene sulphonic acid (65%-solution in water) and 0.2 moles of sodium hydroxide (50%-solution in water) there was added dropwise over a period of 10-25 minutes 0.1 mole of alkylchloroformate at a temperature not higher than 40° C. Subsequently, the temperature of the reaction mixture was increased. After termination of the reaction 50 ml of a saturated aqueous solution of sodium chloride were added, after which the product was filtered off and dried at 120° C.

All products were isolated as white powders and their structure was confirmed by IR and NMR analyses. The sulphonate contents were determined by titration with Hyamine 1622 (from BDH, Great Britain) in chloroform/water using as indicators dimidimium bromide and disulfine blue. The yields were calculated on the amount of 4-hydroxybenzene sulphonic acid.

TABLE

| Compound No | alkyl group | reaction temp (°C.) | reaction time (h) | sulphonate content | yield (%) |
|---|---|---|---|---|---|
| 1 | n-hexyl | 80 | 1.25 | 80.1 | 84.3 |
| 2 | 2-ethylhexyl | 85 | 0.5 | 82.4 | 65.5 |
| 3 | n-decyl | 80 | 1 | 74.1 | 64.8 |

In a similar manner p-sulphophenyl n-octyl carbonate (compound 4) was prepared, starting from 2 moles of 4-hydroxybenzene sulphonic acid. The reaction temperature and reaction time employed were 80° C. and 1.5 h, respectively; the product obtained had a sulphonate content of 97.3% and was isolated in a yield of 70.8%.

EXAMPLE 2

The compounds 1, 2 and 3 were tested for their bleach activating action as follows.

An Imidial Grün piece of test cloth (from the laundry research institute Krefeld, West-Germany) of 9×9 cm was treated for 30 minutes at 60° C. with 300 ml of an aqueous (14° GH) solution containing per liter 0.4 g of sodium percarbonate (corresponding to 3.4 mmoles of hydrogen peroxide), 1.5 g of sodium tripolyphosphate and 1.4 mmoles of bleaching activator. Subsequently, the piece of cloth was rinsed in tap water and dried to the air. The amount of colorant left on the piece of cloth was determined with the aid of a reflectometer by measuring the light reflected in all directions at an angle of 45° of a beam of tristimulus blue light directed perpendicular to the piece of cloth.

The value found was compared with that determined on a non-washed piece of cloth and the difference expressed in the value $\Delta R$; the higher this value, the better the bleaching action and, hence, the effectiveness of the activator.

The $\Delta R$ values found for the present compounds 1, 2 and 3 are: 13.7, 9.6 and 4.8 respectively.

In a comparative experiment conducted with 1.4 mmoles/l sodium p-sulphophenyl ethyl carbonate, an activator according to U.S. Pat. No. 3,272,750, the $\Delta R$ value was found to be 0.9.

These results are clearly proof of the good bleach activating action of the compounds according to the invention.

Further of compounds 1, 2 and 3 the bleach activating action was tested in the above-described manner and in the presence of different amounts of a surfactant mixture containing 80% of a linear alkyl benzene sulphonate and 20% of an ethoxylated (11EO) fatty alcohol. The aqueous solutions with which the pieces of test cloth were treated contained per liter 1 g of sodium percarbonate (corresponding to 8.4 mmoles of hydrogen peroxide), 2 g of sodium tripolyphosphate, 0.5 g of sodium disilicate, 0.25 g of a 25%-solution in water of ethylene diamine tetramethylene phosphonic acid pentasodium salt (Dequest 2046, a commercial product of Monsanto) and 1.7 mmoles of the compounds 1, 2 or 3. The pH of the solutions was 9.5-9.9 and the treating temperature 40° C. The amount of surfactant was 0, 0.35 or 0.70 g per liter. The $\Delta R$ values found for these three different amounts were, respectively:
of compound 1: 6.7, 6.6 and 6.8;
of compound 2: 5.7, 5.6 and 4.8;
of compound 3: 2.8, 3.2 and 2.8.
These values show that the activator action of the present compounds is practically not influenced by the presence of a surfactant.

EXAMPLE 3

Use being made of the same procedure as described in Example 2, the activator action of sodium p-sulphophenyl 2-ethylexyl carbonate (compound No. 2) in the presence of a standard detergent was determined as a function of time and temperature. The standard detergent was of the following composition:
8% sodium linear alkyl (average $C_{11\frac{1}{2}}$) benzene sulphonate;
2.9% ethoxylated (14 EO) talc alcohol;
3.5% sodium soap (13-26% $C_{12-16}$; 74-78% $C_{18-22}$)
43.7% sodium triphosphate
7.5% sodium silicate ($SiO_2$: $Na_2O = 3,3:1$), 1.9% magnesium silicate;
1.2% carboxymethyl cellulose;
0.3% sodium ethylene diamine tetraacetate,
0.3% optical whitening agent for cotton (stilbene type);
21% sodium sulphate;
9.7% water.

Imidial Grün pieces of cloth of 7×9 cm were treated for 10, 20 and 30 minutes at 40° C. and 60° C. with 150 ml of an aqueous (9° GH) solution containing per liter 5.16 g of the standard detergent, 0.69 g of sodium perborate (corresponding to 8.75 mmoles of hydrogen peroxide), 0.25 g of Dequest 2046 and 1.68 mmoles of bleaching activator. The pH of the solution was 10.12. The values found for ΔR were successively:
at 40° C.: 2.2, 3.5 and 3.5;
at 60° C.: 4.3, 5.5 and 5.4.

In a comparative experiment the values found for sodium p-sulphophenyl ethyl carbonate, an activator according to U.S. Pat. No. 3,272,750 were:
at 40° C.: 0.2, 1.3 and 1.5;
at 60° C.: 1.3, 1.5 and 2.1.
This example shows that throughout the treatment both at 40° C. and 60° C. the activating effectiveness of the compound according to the invention is better than that of the prior art activator.

EXAMPLE 4

Using an analogous procedure as described in Example 3, three sodium p-sulphophenyl alkyl carbonates according to the invention (compounds 1, 2 and 4) were compared for their bleach activating action with sodium p-sulphophenyl ethyl carbonate and sodium p-sulphophenyl n-butyl carbonate, both activators according to U.S. Pat. No. 3,272,750.

Imidial Grün pieces of test cloth (5×5 cm) were treated for 30 minutes at 40° C. and 60° C. with 150 ml of an aqueous (5° GH) solution containing per liter 5.16 g of the standard detergent, 0.69 g of sodium perborate and the amounts of bleaching activator as indicated in the Table below. The values found for ΔR are also given in the Table. In these experiments the values for ΔR were determined by comparing the reflectometer results with those found on test cloths washed under similar conditions but without a bleaching activator present in the wash solution.

TABLE

| | ΔR values | | |
| --- | --- | --- | --- |
| | Temperature (°C.) | | |
| | 40 | 60 | 60 |
| | Activator concentration (mmoles/l) | | |
| Alkyl group | 1.67 | 1.67 | 2.50 |
| ethyl[1] | 0.6 | 1.5 | 3.6 |
| n-butyl[1] | 3.9 | 3.5 | 5.8 |
| n-hexyl | 7.7 | 8.5 | 11.4 |
| n-octyl | 7.8 | 8.6 | 10.4 |
| 2-ethylhexyl | 7.0 | 8.3 | 8.8 |

[1]According to U.S. Pat. No. 3,272,750

The results in the Table clearly demonstrate the effectiveness of the bleaching activators according to the invention as compared with that of the prior art activators.

We claim:
1. A compound of the general structural formula

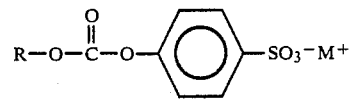

where R is an alkyl group and M+ represents a cation, and that the alkyl group contains 6 to 8 carbon atoms, with the proviso that the $C_6$-alkyl group is n-hexyl.

2. A compound according to claim 1, wherein the alkyl group is n-hexyl, n-octyl or 2-ethylhexyl.

3. A detergent additive comprising a bleaching activator and a solid carrier, wherein the bleaching activator is a compound according to claim 1.

4. A detergent additive according to claim 3, wherein the carrier is sodium chloride, sodium sulphate or a mixture thereof.

5. A detergent composition containing a surfactant, a bleaching activator and a bleaching agent generating hydrogen peroxide under alkaline conditions, wherein the bleaching activator is a compound according to claim 1.

6. A compound of the structural formula

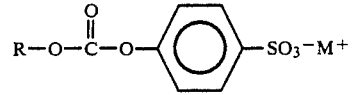

where R is an alkyl group and M+ represents a cation, and the alkyl group contains 6 to 10 carbon atoms, with the proviso that the $C_6$-alkyl group is n-hexyl.

7. A compound according to claim 6, wherein the alkyl group is n-hexyl.

8. A compound according to claim 6, wherein the alkyl group is n-octyl.

9. A compound according to claim 6, wherein the alkyl group is 2-ethylhexyl.

10. A compound according to claim 6, wherein the alkyl group is 3,5,5-trimethylhexyl.

11. A compound according to claim 6, wherein the alkyl group is n-decyl.

12. A composition comprising a mixture of compounds of claim 6.

* * * * *